(12) United States Patent
Rode et al.

(10) Patent No.: US 11,460,407 B2
(45) Date of Patent: Oct. 4, 2022

(54) SAMPLE-BASED GAS QUALITY CONTROL BY MEANS OF RAMAN SPECTROSCOPY

(71) Applicants: CARL ZEISS JENA GMBH, Jena (DE); CARL ZEISS SPECTROSCOPY GMBH, Jena (DE)

(72) Inventors: Michael Rode, Jena (DE); Alexandre Gatto, Jena Münchenroda (DE); Arnaud Deparnay, Erfurt (DE); Michael Helgert, Jena (DE)

(73) Assignees: Carl Zeiss Jena GmbH, Jena (DE); Carl Zeiss Spectroscopy GmbH, Jena (DE)

( * ) Notice: Subject to any disclaimer, the term of this patent is extended or adjusted under 35 U.S.C. 154(b) by 305 days.

(21) Appl. No.: 16/636,281

(22) PCT Filed: Aug. 2, 2018

(86) PCT No.: PCT/EP2018/071047
§ 371 (c)(1),
(2) Date: Feb. 3, 2020

(87) PCT Pub. No.: WO2019/025564
PCT Pub. Date: Feb. 7, 2019

(65) Prior Publication Data
US 2021/0164907 A1    Jun. 3, 2021

(30) Foreign Application Priority Data
Aug. 4, 2017   (DE) .................... 10 2017 117 709.4

(51) Int. Cl.
*G01N 21/65* (2006.01)
*F24F 11/63* (2018.01)
(Continued)

(52) U.S. Cl.
CPC ............. *G01N 21/65* (2013.01); *B60H 1/008* (2013.01); *F24F 11/63* (2018.01);
(Continued)

(58) Field of Classification Search
USPC .......................................................... 702/24
See application file for complete search history.

(56) References Cited

U.S. PATENT DOCUMENTS

| 3,768,908 A | 10/1973 | Zaromb |
| 5,866,430 A | 2/1999 | Grow |

(Continued)

FOREIGN PATENT DOCUMENTS

| CN | 104459058 A | 3/2015 |
| CN | 204666187 U | 9/2015 |

(Continued)

OTHER PUBLICATIONS

International Search Report and Written Opinion of the International Searching Authority, International Application No. PCT/EP2018/071047, dated Oct. 22, 2018, 9 pp.
(Continued)

*Primary Examiner* — Paul D Lee
(74) *Attorney, Agent, or Firm* — Myers Bigel, P.A.

(57) ABSTRACT

For the purpose of gas quality monitoring, a spectroscopic examination of a gas sample from a space (10) to be monitored is carried out, e.g. by Raman spectroscopy. The spectroscopic examination yields a measurement spectrum extending over a wavelength range. A deviation of the measurement spectrum from at least one comparison sample (160) is then detected. Depending on the detected deviation, a gas quality warning (QW) is produced.

14 Claims, 7 Drawing Sheets

(51) Int. Cl.
    *B60H 1/00*     (2006.01)
    *G01N 33/00*     (2006.01)
    *G06N 3/04*     (2006.01)
    *G06N 3/08*     (2006.01)
    *F24F 110/50*     (2018.01)

(52) U.S. Cl.
    CPC ..... *G01N 33/0027* (2013.01); *G01N 33/0063* (2013.01); *G06N 3/04* (2013.01); *G06N 3/08* (2013.01); *F24F 2110/50* (2018.01); *G01N 2201/06113* (2013.01)

(56) References Cited

U.S. PATENT DOCUMENTS

| | | | |
|---|---|---|---|
| 6,134,004 | A | 10/2000 | Reagen et al. |
| 6,387,706 | B1 | 5/2002 | Eden |
| 6,439,040 | B1 | 8/2002 | Garms et al. |
| 6,552,793 | B1 * | 4/2003 | Kastner .............. G01N 21/3504 250/343 |
| 10,948,404 | B2 * | 3/2021 | Kester ................ G01N 21/3504 |
| 2003/0015019 | A1 | 1/2003 | O'Brien |
| 2005/0247868 | A1 | 11/2005 | Call et al. |
| 2005/0280814 | A1 | 12/2005 | Iuliano |
| 2007/0242275 | A1 | 10/2007 | Spartz et al. |
| 2009/0248342 | A1 | 10/2009 | Hlavaty |
| 2011/0208462 | A1 | 8/2011 | Maier et al. |
| 2014/0052003 | A1 * | 2/2014 | Jiang .................. G01N 21/274 600/475 |
| 2014/0238107 | A1 | 8/2014 | Chou et al. |
| 2015/0092194 | A1 | 4/2015 | Waldmann et al. |
| 2016/0132617 | A1 * | 5/2016 | Liu .................... G06F 30/20 703/2 |

FOREIGN PATENT DOCUMENTS

| | | |
|---|---|---|
| DE | 195 18 598 A1 | 11/1996 |
| DE | 195 28 960 A1 | 2/1997 |
| DE | 196 15 365 A1 | 10/1997 |
| DE | 197 43 954 A1 | 6/1999 |
| DE | 699 24 88 T2 | 3/2006 |
| EP | 2857811 A1 | 4/2015 |
| TW | M422070 U | 2/2012 |
| TW | M500247 U | 5/2015 |
| WO | 97/06424 A1 | 2/1997 |
| WO | 2008/051202 A2 | 5/2008 |
| WO | 2014/134521 A1 | 9/2014 |

OTHER PUBLICATIONS

Search Report, DE Application No. 10 2017 117 709.4, dated Mar. 26, 2018, 12 pp.
Asano, "Measurement Systems for Diesel Exhaust Gas and Future Trends", Horiba Technical Reports, Dec. 20, 2001, pp. 12-16.
Carslaw et al., "New insights from comprehensive on-road measurements of Nox, No2 and NH3 from vehicle emission remote sensing in London, UK", Atmospheric Environment, vol. 81, Dec. 2013, pp. 339-347.
Che et al., "Determination of Volatile Compounds in Automotive Interior Materials by Thermal Desorption GC-MS", Thermo Scientific Application Note 10363, (c) 2014, 5 pp.
Crypton Diagnostic Equipment, "Understanding Exhaust Emissions", downloaded Jan. 22, 2020 from http://www.crypton.co.za/Tto%20know/Emissions/exhaust%20emissions.html, 5 pp.
Ebermann et al., "Spektral abstimmbare IR-Sensoren fur die industrielle Prozessmesstechnik und die medizinische Gasanalyse", Technisches Messen, vol. 79, No. 10, Oct. 2012, pp. 440-450.
Goodacre, "Explanatory analysis of spectroscopic data using machine learning of simple, interpretable rules", Vibrational Spectroscopy, vol. 32, No. 1, Aug. 2003, pp. 33-45.
Infrared Industries, "HM5000 Handheld Gas Analyzer" downloaded Jan. 22, 2020 from http://www.infraredindustries.com/product/hm5000-handheld-gas-analyzer/, (c) 2020, 2 pp.
Keison Products, "Kane Auto 1 Single Gas Emission Analyser", downloaded Jan. 22, 2020 from http://www.keison.co.uk/kane_auto1.shtml, 2 pp.
Leidinger et al., "Detektion von CO2 und fluchtigen organischen Komponenten mittels Kombination von Halbleiter-Gassensorik und Infrarotspektroskopie", Dresdner Sensor Symposium 2013, Dec. 9, 2013-Dec. 11, 2013, pp. 229-233.
Nova Gas, "Portable Exhaust Analyzers", downloaded Jan. 22, 2020 from http://www.nova-gas.com/analyzers/engine-exhaust, 6 pp.
TSI Incorporated, "Combustion Analysis Basics: An Overview of Measurements, Methods and Calculations Used in Combustion Analysis", P/N 2980175, 2004, 35 pp.
Klingenberg et al., "Multicomponent Automobile Exhaust Measurements", from Monitoring of Gaseous Pollutants by Tunable Diode Lasers (ed. Grisar et al.), Proceedings of the International Symposium held in Freiburg, DE, Nov. 13-14, 1986 pp. 108-115.

* cited by examiner

SAMPLE-BASED GAS QUALITY CONTROL BY MEANS OF RAMAN SPECTROSCOPY

CROSS REFERENCE TO RELATED APPLICATIONS

This application is a 35 U.S.C. § 371 national stage application of PCT International Application No. PCT/EP2018/071047, filed on Aug. 2, 2018, which itself claims the benefit of and priority to German Application No. 10 2017 117 709.4, filed Aug. 4, 2017, the disclosure and content of both of which are incorporated by reference herein in their entireties.

BACKGROUND

The present application relates to methods and apparatuses for spectroscopic gas quality monitoring.

In various fields, there is an interest in monitoring gases with regard to their composition. In this regard, by way of example, by monitoring air in the open or in closed spaces, a deterioration in air quality caused by environmental pollution can be detected. However, a deterioration in air quality can also occur independently of environmental pollution influences for example in the interior of an aircraft if a contaminant is introduced in the course of obtaining compressed air for ventilating the interior from bleed air from engines. Furthermore, in air conditioning or ventilation installations, too, there is the risk of contamination of the air by substances used in the installation, e.g. oil or coolant, or by foreign substances introduced into the installation.

Existing systems for air quality monitoring are typically based on an analysis of the air with regard to specific pollutants, e.g. ozone, $CO_2$, CO, sulfur oxides, nitrogen oxides or fine dust. WO 2014/134521 A1 describes for example a system in which the concentrations of various target pollutants are detected and evaluated. However, the analysis system required for measuring concentrations of individual pollutants is complex and typically sensitive to variable ambient conditions. Furthermore, unexpected pollutants might occur, too, for the detection of which the analysis system is not designed.

SUMMARY

It is therefore an object of the present invention to provide techniques which enable efficient gas quality monitoring.

A method for gas quality monitoring and an apparatus for gas quality monitoring are provided for this purpose.

In accordance with one exemplary embodiment of the present invention, a method for gas quality monitoring is thus provided. The method comprises a spectroscopic examination of a gas sample from a space to be monitored. The spectroscopic examination can be carried out in particular by Raman spectroscopy. The spectroscopic examination yields a measurement spectrum extending over a wavelength range. Furthermore, a deviation of the measurement spectrum from at least one comparison pattern is detected. Depending on the detected deviation, a gas quality warning is produced. In particular, the gas quality warning is produced if a deviation of the measurement spectrum from the comparison pattern or one of the comparison patterns occurs or the detected deviation has a specific minimum severity. The comparison pattern can describe shared properties of measurement spectra classified as inconspicuous. The at least one comparison pattern can thus be produced on the basis of measurement spectra that were obtained by examination of gas samples classified as inconspicuous. In the event of a deviation from the properties described by the comparison pattern, the measurement spectrum obtained by the spectroscopic examination can be classified as conspicuous and the gas quality warning can be produced. The gas quality warning can thus be produced in an efficient manner, without a composition or individual constituents of the gas sample having to be identified.

In accordance with one exemplary embodiment, furthermore, at least one ambient parameter of the space to be monitored is detected. The at least one comparison pattern can be selected depending on the at least one ambient parameter detected. The at least one ambient parameter can comprise a temperature, a pressure and/or a moisture content in the space to be monitored. As a result of selecting the at least one comparison pattern depending on the at least one ambient parameter, variable ambient conditions can be taken into account in an efficient manner. In particular, respectively appropriate comparison patterns can be used for different ambient conditions.

In accordance with one exemplary embodiment, the deviation is detected by a comparison of a wavelength-dependent intensity of the measurement spectrum with at least one comparison intensity defined by the comparison pattern. In this regard, the at least one comparison pattern can define for example a wavelength-dependent comparison intensity, the exceedance of which constitutes a deviation from the comparison pattern. In a similar manner, the at least one comparison pattern can define a wavelength-dependent comparison intensity, the undershooting of which constitutes a deviation from the comparison pattern. The comparison pattern can thus define in a wavelength-dependent manner an intensity range within which the measurement spectrum is classified as inconspicuous and no gas quality warning is produced.

In accordance with one exemplary embodiment, the measurement spectrum is represented in the form of an image, which is subdivided into a first region and a second region depending on a wavelength-dependent intensity. The deviation can then be detected by detecting an overlap of the first region and/or of the second region with at least one comparison region defined by the comparison pattern. By way of example, the at least one comparison pattern can define a comparison region for which an overlap with the first region of the measurement spectrum represents a deviation from the comparison pattern. In a similar manner, the at least one comparison pattern can define a comparison region for which an incomplete or absent overlap with the first region of the measurement spectrum represents a deviation from the comparison pattern. In this exemplary embodiment, the deviation can be detected in an efficient manner using image evaluation techniques.

In accordance with an exemplary embodiment, furthermore, a severity of the deviation is detected and the gas quality warning is produced depending on the detected severity of the deviation. By way of example, the severity of the deviation can be compared with a threshold value and the gas quality warning can be produced if the severity of the deviation exceeds the threshold value. However, it is also possible to compare the severity of the deviation with a plurality of threshold values. In this regard, by way of example, a first level of the gas quality warning can be produced if the severity of the deviation exceeds a lower threshold value, and a second level of the gas quality warning can be produced if the severity of the deviation exceeds an upper threshold value.

In accordance with an exemplary embodiment, an apparatus for conveying gas into the space to be monitored and/or out of the space to be monitored is controlled depending on the gas quality warning produced. By way of example, the apparatus can comprise a ventilation installation. The space to be monitored can then be situated in an air feed section of the ventilation installation or in a space to be ventilated by way of the ventilation installation. In accordance with a further example, the apparatus can comprise a process installation. In this case, the space to be monitored can be situated in a feed section for a process gas used in the process installation or can be situated in a process space of the process installation.

In accordance with a further exemplary embodiment of the present invention, an apparatus for gas quality monitoring is provided. The apparatus comprises a spectrometer device for the spectroscopic examination of a gas sample from a space to be monitored. The spectroscopic examination yields a measurement spectrum extending over a wavelength range. Furthermore, the apparatus comprises an evaluation device. The evaluation device is configured to detect a deviation of the measurement spectrum from at least one comparison pattern. Furthermore, the evaluation device is configured to produce a gas quality warning depending on the detected deviation. The apparatus for gas quality monitoring can thus be configured for carrying out the method according to any of the above exemplary embodiments.

In accordance with a further exemplary embodiment of the present invention, a ventilation installation is provided. The ventilation installation serves for ventiling a space, e.g. an interior of a vehicle or of a building. The ventilation installation can also be part of an air conditioning system, for example. The ventilation installation comprises an apparatus for conveying air into the space to be ventilated and/or out of the space to be ventilated. Furthermore, the ventilation installation comprises an apparatus for gas quality monitoring in accordance with the above exemplary embodiment. In this case, the space to be monitored can be situated in an air feed section of the ventilation installation or in the space to be ventilated. Furthermore, in this case, the apparatus for conveying air can be controlled depending on the gas quality warning. In this regard, by way of example, depending on the gas quality warning, the feed of air into the space to be ventilated can be stopped and/or intensified venting of the space can be instigated.

In accordance with a further exemplary embodiment of the present invention, a process installation is provided. The process installation comprises an apparatus for conveying gas into a process space of the process installation and/or out of the process space of the process installation. Furthermore, the process installation comprises an apparatus for gas quality monitoring in accordance with the above exemplary embodiment. In this case, the space to be monitored can be situated in a feed section for a process gas used in the process installation or can be situated in the process space of the process installation. Furthermore, in this case, too, the apparatus for conveying gas can be controlled depending on the gas quality warning. In this regard by way of example, depending on the gas quality warning, the feed of a deficient process gas can be stopped and/or an intensified discharge of gas out of the process space can be instigated. Furthermore, gas purification can also be instigated, e.g. by activating a filter device or initiating a chemical purification process.

For an improved understanding, exemplary embodiments are explained in greater detail below with reference to the accompanying drawings.

DETAILED DESCRIPTION

Various exemplary embodiments are explained in greater detail below. However, this detailed description should not be construed as restrictive. In particular, a description of an exemplary embodiment with a multiplicity of features, components or details should not be interpreted to the effect that all these features, components and details are necessary for implementation. Variations and modifications that have been described for one of the exemplary embodiments are also applicable to other exemplary embodiments, unless indicated otherwise. Moreover, features of different exemplary embodiments can be combined with one another in order to form further exemplary embodiments.

Figure 1:
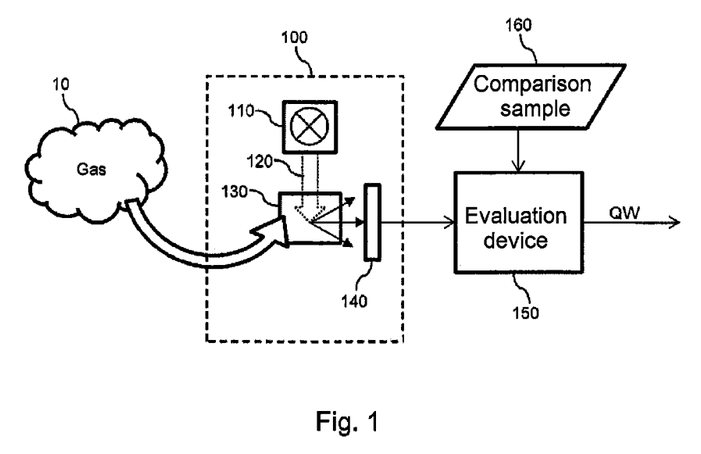
FIG. 1 schematically illustrates an apparatus for gas quality monitoring in accordance with an exemplary embodiment of the invention.

The exemplary embodiments explained below relate to gas quality monitoring in association with a ventilation installation or a process installation. FIG. 1 schematically illustrates an apparatus for gas quality monitoring that is used for this purpose.

As illustrated in FIG. 1, the apparatus comprises a spectrometer device 100 and an evaluation device 150. The spectrometer device serves for the examination of gas samples from a space 10 to be monitored. The gas samples to be examined can be taken at short time intervals, e.g. of the order of magnitude of one second or less, in order thus to enable quasi-continuous monitoring of the gas quality. The space 10 to be monitored can be for example an interior of a building or of a vehicle. Furthermore, the space 10 to be monitored can be an air feed section or an exhaust air section of a ventilation installation for a building or a vehicle. Furthermore, the gas samples could also be taken in the open. In these application scenarios, a gas contained in the space 10 would be air, i.e. the apparatus would be used for monitoring air quality. In other application scenarios, the apparatus can be used in association with a process installation. In this case, the space 10 to be monitored can be a process space, e.g. a combustion chamber or an etching chamber, part of a line for a process gas used in the process installation, or part of an exhaust gas line. In the last-mentioned application scenarios, the gas contained in the space 10 would be a process gas or exhaust gases of a process.

In the example illustrated, the spectrometer device 100 is configured as a Raman spectrometer and comprises a radiation source 110, which generates excitation light 120. The radiation source 110 can be a laser, for example. Furthermore, the spectrometer device has a measurement chamber 130, into which the gas samples to be examined are introduced. This can be done for example by way of a pump system, not illustrated in the figure. The excitation light 120 is radiated into the measurement chamber 130 and light scattered in the measurement chamber 130 is detected by a detector 140 in order thus to obtain a measurement spectrum for each gas sample. The measurement spectra are then fed to the evaluation device 150 for further analysis.

The evaluation device 150 compares the measurement spectra with a comparison pattern 160 in order to ascertain a deviation of the respective measurement spectrum from the comparison pattern 160. The comparison pattern 160 is based on shared properties of measurement spectra which were previously classified as inconspicuous. In some cases, it is also possible to compare the measurement spectrum with a plurality of comparison patterns 160. If the evaluation device 150 ascertains a deviation of the measurement spectrum from the comparison pattern 160 or if the ascertained deviation exceeds a specific minimum severity, the evaluation device 150 produces a gas quality warning QW. The gas quality warning QW can be a signal which indicates a risk of inadequate gas quality. The gas quality warning QW can be configured for example as an optical or acoustic signal for directly warning persons. Furthermore, the gas quality warning QW can also be an electronic signal, however, which triggers automated control processes.

In order to ensure a compact construction of the spectrometer device 100, imaging diffraction gratings can be used in the detector 140, said gratings realizing, in one component, both a spectral decomposition of the scattered light and an imaging onto a line or an array of light-sensitive elements. Said imaging diffraction gratings can for example be produced with a diameter of 10 mm or less by means of a holographic method and be integrated monolithically in the spectrometer device 100 by means of an injection-molding method. Furthermore, the measurement chamber 130 could also be combined with a cavity for amplifying the excitation light 120. By means of one or more of these measures, it is possible to achieve a compact construction of the spectrometer device 100 with a volume of a few cm³. This last is advantageous particularly in the case of use in the field of vehicles. However, a compact design of the spectrometer device 100 can also be advantageous in ventilation installations of buildings or in process installations because this facilitates for example an arrangement of the spectrometer device 100 near to the location at which the gas sample is taken. In this way, it is possible in turn to prevent latency times and dead volumes from adversely affecting the gas quality monitoring.

Figure 2:
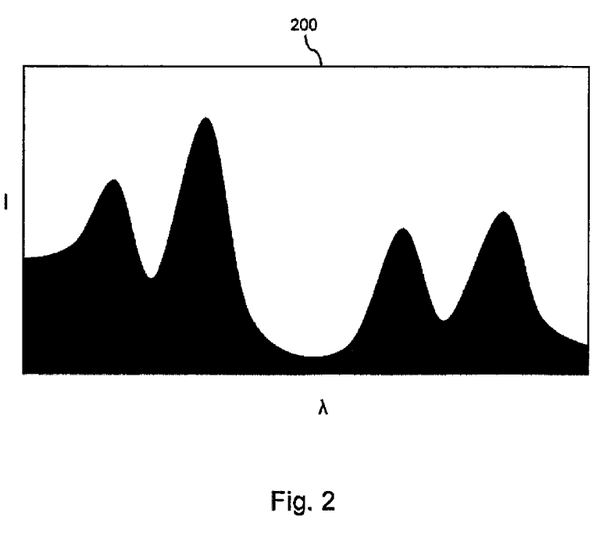
FIG. 2 shows an example of a measurement spectrum which can be used for gas quality monitoring in accordance with an exemplary embodiment of the invention.

FIG. 2 shows an exemplary measurement spectrum 200 detected by the detector 140. As illustrated in FIG. 2, the measurement spectrum shows an intensity I of the detected scattered light as a function of the wavelength A. However, it goes without saying here that the dependence on the wavelength A can also be represented as dependence on frequency or wavenumber in an equivalent manner. The term "wavelength-dependent" used here should thus be understood to be synonymous with "frequency-dependent" or "wavenumber-dependent". In this case, a wavelength range covered by the measurement spectrum 200 can be in the range of 100 nm to 3000 nm. The measurement spectrum 200 can be for example a measurement spectrum in the ultraviolet range of approximately 180 nm to approximately 400 nm, a measurement spectrum in the visible range of approximately 380 nm to approximately 800 nm, a measurement spectrum in the near infrared range of approximately 700 nm to approximately 2500 nm, a combination of two or more of these ranges, or parts of these ranges.

The measurement spectrum 200 illustrated by way of example in FIG. 2 does not show any sharp lines, but rather a profile having a plurality of bands, which additionally also shows a certain background intensity. This profile is typical of a scenario in which the gas sample examined is a mixture of different gases and moreover can also contain liquid or solid particles. In such scenarios, an identification of individual constituents of this gas mixture on the basis of the measurement spectrum is typically extremely complex or, under certain circumstances, not possible at all. Furthermore, even in the case of a specific composition of the gas sample, the measurement spectrum 200 can have a considerable variability depending on ambient parameters such as temperature, pressure or moisture content. This additionally hampers an identification of individual constituents of the gas mixture. Therefore, the gas quality monitoring described herein is not based on an identification of individual constituents of the gas sample examined, but rather on the already mentioned detection of deviations of the measurement spectrum 200 from one or a plurality of comparison patterns. This will be explained in greater detail below on the basis of examples.

Figure 3A:
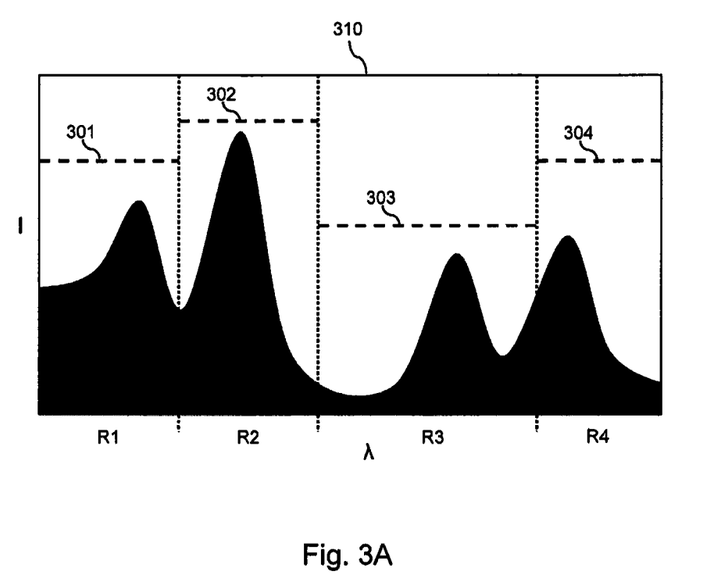
FIGS. 3A and 3B illustrate an example of an evaluation of deviations between a measurement spectrum and a comparison pattern in accordance with an exemplary embodiment of the invention.
Figure 3B:
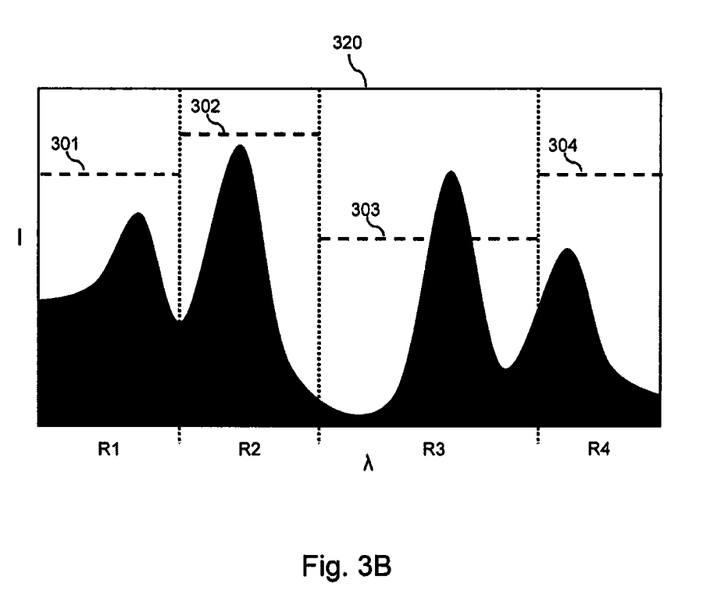

FIGS. 3A and 3B illustrate an example of an evaluation of a deviation between a measurement spectrum 310, 320 and a comparison pattern, which defines a plurality of wavelength-dependent comparison intensities 301, 302, 303, 304. In the case of the example in FIGS. 3A and 3B, the comparison intensities 301, 302, 303, 304 include a first comparison intensity 301 in a first wavelength range R1, a second comparison intensity 302 in a second wavelength range R2, a third comparison intensity 303 in a third wavelength range R3, and a fourth comparison intensity 304 in a fourth wavelength range R4, which differ from one another. In this example, the comparison intensities 301, 302, 303, 304 each correspond to a maximum intensity, the exceedance of which is classified as a deviation from the comparison pattern. A corresponding maximum intensity can be determined for example by the evaluation of measurement spectra classified as inconspicuous, by ascertaining for the measurement spectra classified as inconspicuous the maximum observed intensity value in the respective wavelength range R1, R2, R3, R4.

In the case of the scenario illustrated in FIG. 3A, the intensity values of the measurement spectrum 310 do not exceed the comparison intensities 301, 302, 303, 304 in any of the wavelength ranges R1, R2, R3, R4. In this case, therefore, no deviation from the comparison pattern is ascertained and the gas quality warning QW is not produced. In the case of the scenario illustrated in FIG. 3B, however, the intensity values of the measurement spectrum 320 exceed the corresponding comparison intensity 303 in the wavelength range R3. In this case, therefore, a deviation from the comparison pattern is ascertained and the gas quality warning QW is produced.

Figure 4A:
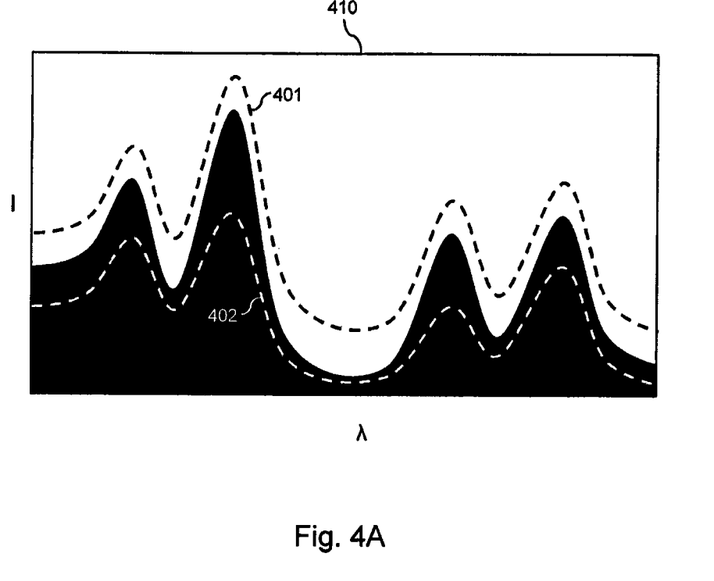
FIGS. 4A and 4B illustrate a further example of an evaluation of deviations between a measurement spectrum and a comparison pattern in accordance with an exemplary embodiment of the invention.
Figure 4B:
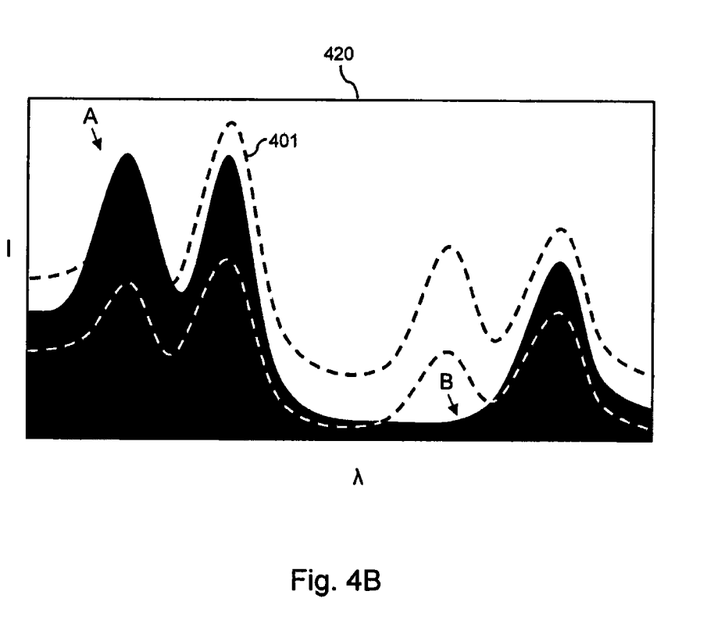

FIGS. 4A and 4B illustrate a further example of an evaluation of a deviation between a measurement spectrum 410, 420 and a comparison pattern, which defines a plurality of wavelength-dependent comparison intensities 401, 402. In the case of the example in FIGS. 4A and 4B, the comparison intensities 401 include a first wavelength-dependent comparison intensity profile 401 and a second wavelength-dependent comparison intensity profile 402. In this example, the first comparison intensity profile 401 corresponds to a wavelength-dependent maximum intensity, the exceedance of which is classified as a deviation from the comparison pattern. The second comparison intensity profile 402 corresponds to a wavelength-dependent minimum intensity, the undershooting of which is classified as a deviation from the comparison pattern. The wavelength-dependent comparison intensity profile 401 can be determined for example by the evaluation of measurement spectra classified as inconspicuous, by ascertaining an upper envelope of the measurement spectra classified as inconspicuous. The wavelength-dependent comparison intensity profile 402 can be determined for example by the evaluation of measurement spectra classified as inconspicuous, by ascertaining a lower envelope of the measurement spectra classified as inconspicuous.

In the case of the scenario illustrated in FIG. 4A, the intensity values of the measurement spectrum 410 do not exceed the comparison intensity profile 401 at any wavelength λ. Furthermore, the intensities values of the measurement spectrum 410 also do not undershoot the comparison intensity profile 402 at any wavelength λ. In this case, therefore, no deviation from the comparison pattern is ascertained and the gas quality warning QW is not produced. In the case of the scenario illustrated in FIG. 4B, however, the intensity values of the measurement spectrum 420 exceed the comparison intensity profile 401 in a region identified by A and undershoot the comparison intensity profile 402 in a region identified by B. In this case, therefore, a deviation from the comparison pattern is ascertained and the gas quality warning QW is produced. It goes without saying here that the exceedance at A and the undershooting at B can each be interpreted individually as a deviation and can also trigger the production of the gas quality warning QW independently of one another. In the case of the example in FIGS. 4A and 4B, it furthermore goes without saying that the wavelength-dependent comparison intensity profiles 401 and 402 can also be used separately as comparison patterns.

Figure 5A:
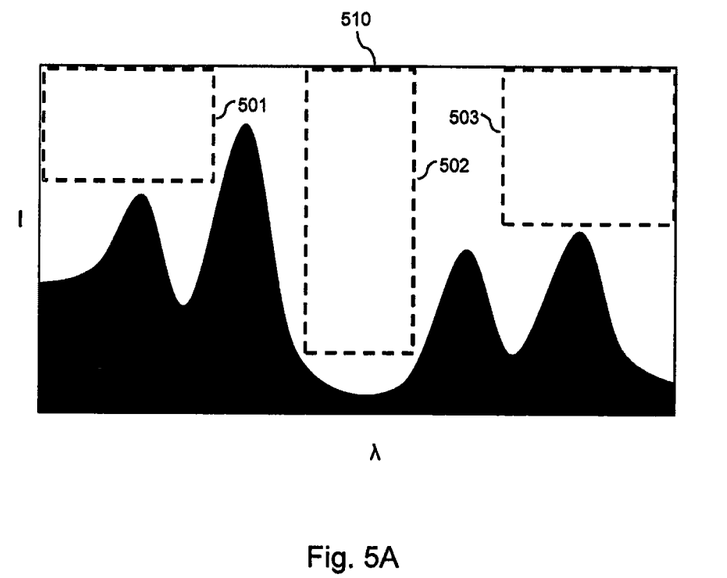
FIGS. 5A and 5B illustrate a further example of an evaluation of deviations between a measurement spectrum and a comparison pattern in accordance with an exemplary embodiment of the invention.
Figure 5B:
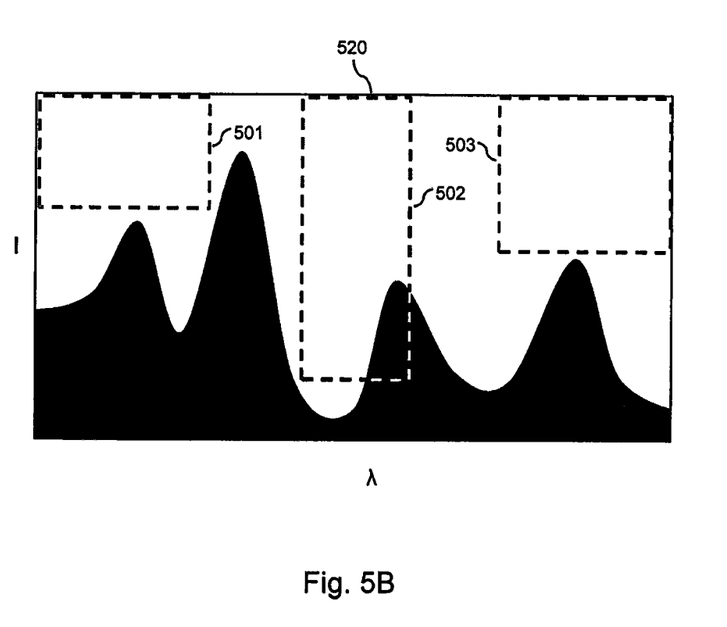

FIGS. 5A and 5B illustrate a further example of an evaluation of a deviation between a measurement spectrum 510, 520 and a comparison pattern. This example makes use of the fact that the measurement spectrum 510, 520 is represented as an image, which is subdivided into a first region and a second region by the intensity profile of the measurement spectrum 510, 520. In FIGS. 5A and 5B, the first region is illustrated as a dark area. The second region is illustrated as a bright area above the dark area. In this case, the measurement spectrum can be compared with the comparison pattern on the basis of the image having the two regions. By way of example, image analysis techniques can be used here. Specifically, in the case of the example in FIGS. 5A and 5B, the comparison pattern defines comparison regions 501, 502, 503. An overlap of the first region, illustrated as dark, with one of said comparison regions 501, 502, 503 is classified as a deviation from the comparison pattern. The comparison regions 501, 502, 503 can be determined for example by the evaluation of measurement spectra classified as inconspicuous, by detecting, for images corresponding to these measurement spectra, regions which in all of the images are part of the second region, illustrated as bright. It goes without saying here that the comparison regions 501, 502, 503 need not necessarily have a rectangular shape, as illustrated in FIGS. 5A and 5B, rather other shapes of the comparison regions can also be used, e.g. a triangular shape, irregular polygons or shapes having a curved boundary. Furthermore, it goes without saying that for the second region, illustrated as bright, of the image as well, one or a plurality of comparison regions could be defined for which the fact of whether there is an overlap with the second region of the image is detected.

In the case of the scenario illustrated in FIG. 5A, there is no overlap of the first region, illustrated as dark, with any of the comparison regions 501, 502, 503. In this case, therefore, no deviation from the comparison pattern is ascertained and the gas quality warning QW is not produced. In the case of the scenario illustrated in FIG. 5B, there is an overlap of the first region, illustrated as dark, with the comparison region 502. In this case, therefore, a deviation from the comparison pattern is ascertained and the gas quality warning QW is produced.

Figure 6A:
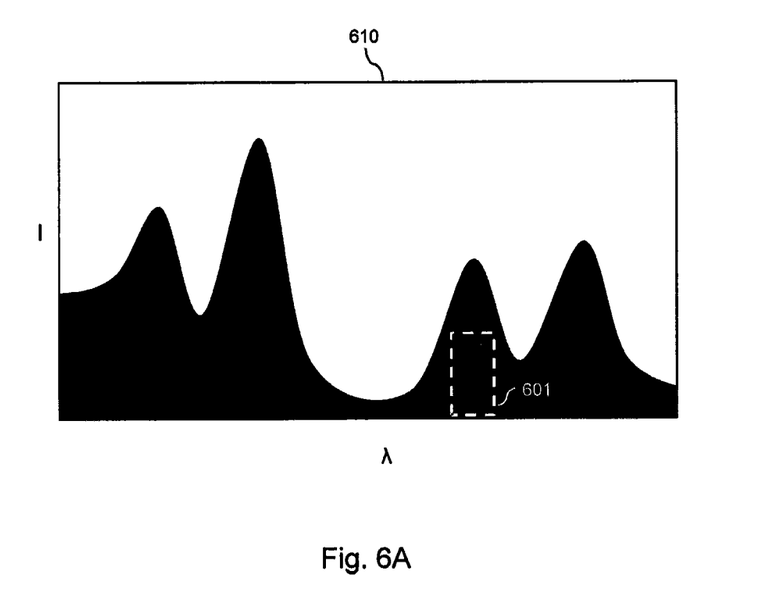
FIGS. 6A and 6B illustrate a further example of an evaluation of deviations between a measurement spectrum and a comparison pattern in accordance with an exemplary embodiment of the invention.
Figure 6B:
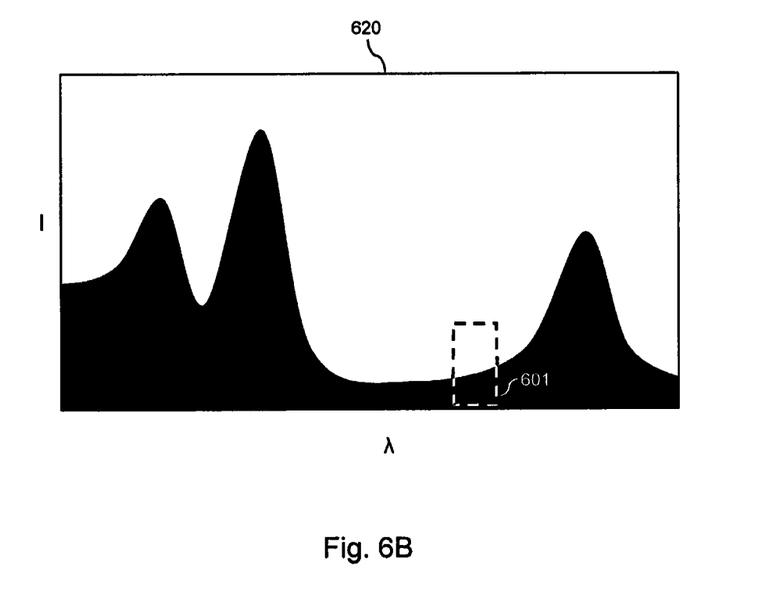

FIGS. 6A and 6B illustrate a further example of an evaluation of a deviation between a measurement spectrum 610, 620 and a comparison pattern. In a manner similar to that in the example in FIGS. 5A and 5B, this example makes use of the fact that the measurement spectrum 610, 620 is represented as an image, which is subdivided into a first region and a second region by the intensity profile of the measurement spectrum 610, 620. In FIGS. 6A and 6B, the first region is illustrated as a dark area. The second region is illustrated as a bright area above the dark area. In a manner similar to the example in FIGS. 5A and 5B in this case, too, the measurement spectrum can be compared with the comparison pattern on the basis of the image having the two regions, e.g. using image analysis techniques. In the case of the example in FIGS. 6A and 6B, the comparison pattern defines a comparison region 601. A lack of a complete overlap of the first region, illustrated as dark, with said comparison region 601 is classified as a deviation from the comparison pattern. The comparison region 601 can be determined for example by the evaluation of measurement spectra classified as inconspicuous, by detecting, for images corresponding to these measurement spectra, regions which in all of the images are part of the first region, illustrated as dark. In this example, too, it goes without saying that the comparison region 601 need not necessarily have a rectangular shape, as illustrated in FIGS. 6A and 6B, rather other shapes can also be used, e.g. a triangular shape, irregular polygons or shapes having a curved boundary. Furthermore, it goes without saying that for the second region, illustrated as bright, of the image as well, one or a plurality of comparison regions could be defined for which the fact of whether an overlap with the second region of the image is complete is detected.

In the case of the scenario illustrated in FIG. 6A, there is a complete overlap of the first region, illustrated as dark, with the comparison region 601. In this case, therefore, no deviation from the comparison pattern is ascertained and the gas quality warning QW is not produced. In the case of the scenario illustrated in FIG. 6B, the overlap of the first region, illustrated as dark, with the comparison region 601 is incomplete. In this case, therefore, a deviation from the comparison pattern is ascertained and the gas quality warning QW is produced It goes without saying that the types of comparison patterns that have been described on the basis of the examples mentioned above can also be combined with one another in any desired manner. In this regard, e.g. in some wavelength ranges comparison intensities could be defined as explained with reference to FIGS. 3A and 3B or FIGS. 4A and 4B and comparison regions could additionally be defined as explained with reference to FIGS. 5A and 5B or FIGS. 6A and 6B.

Furthermore, in the case of the examples mentioned, it is possible to detect not only the presence of a deviation of the measurement spectrum from the comparison pattern, but also a severity of the deviation, i.e. the deviation can be quantified. In the case of the examples in FIGS. 3A, 3B, 4A and 4B, the severity can be determined for example on the basis of a maximum difference between the intensity values of the measurement spectrum and the comparison intensity. In the case of the examples in FIGS. 5A, 5B, 6A and 6B the severity of the deviation can be determined on the basis of an area content of the comparison region that is overlapped by the first region of the measurement spectrum. In these cases, the gas quality warning QW can be produced depending on the severity of the deviation. By way of example, the gas quality warning QW can be produced if the severity of the deviation exceeds a threshold value. Furthermore, the gas quality warning QW can also be produced in a plurality of levels. In this regard, by way of example, a first level of the gas quality warning QW could be produced if the severity of the deviation exceeds a first threshold value, and a second level of the gas quality warning QW could be produced if the severity of the deviation exceeds a second threshold value. Different automated control processes can then also be instigated depending on the multilevel gas quality warning QW.

The comparison patterns used can be selected depending on the desired type of gas quality monitoring. In this regard, by way of example, a contamination of the gas sample can be identified in an efficient manner by way of comparison patterns with maximum intensities, such as e.g. the comparison intensities 301, 302, 303, 304, or the comparison intensity profile 401, or by way of comparison regions with an overlap that is not permitted, such as e.g. the comparison regions 501, 502, 503. Such a contamination can correspond for example to pollutants or undesired odorants in an air sample. Furthermore, an undesired composition of constituents of the gas sample can be identified in an efficient manner by way of comparison patterns with minimum intensities, such as e.g. the comparison intensity profile 401, by way of comparison patterns with maximum intensities, such as e.g. the comparison intensities 301, 302, 303, 304 or the comparison intensity profile 401, by way of comparison regions with an overlap that is not permitted, such as e.g. the comparison regions 501, 502, 503, or by way of comparison regions with a required overlap, such as e.g. the comparison region 601. Such an undesired composition of constituents of the gas sample can correspond for example to an excessively low concentration of a constituent of a process gas or an excessively low proportion of oxygen in air.

As already mentioned, in many application scenarios the detected measurement spectra exhibit a great dependence on ambient parameters. In this regard, in the case of monitoring air, the measurement spectra typically vary depending on temperature, pressure or air pressure and moisture content or air humidity in the space to be monitored. In the case of monitoring a process gas, the measurement spectra may in turn exhibit a dependence on temperature or pressure of the process gas. These dependencies can be taken into account in the evaluation of the measurement spectra, by one or a plurality of the ambient parameters being detected and the comparison pattern that is used for the comparison or the comparison patterns that are used for the comparison being selected depending on the detected ambient parameter. In this regard, by way of example, comparison patterns used at high temperature can be different than those used at low temperature. The ambient parameter or the ambient parameters can be detected by means of a corresponding sensor system, e.g. a temperature sensor, a pressure sensor or an air humidity sensor.

Furthermore, the ambient parameters can be taken into account by detecting and measuring one or more reference lines in the measurement spectra. Such reference lines can be produced and/or varied with regard to intensity or wavelength in a targeted manner by means of the radiation source 110 of the spectrometer device 100 or a separate reference radiation source. The ambient parameter(s) can then be deduced from a known variation of the reference line(s) as a function of the ambient parameter(s). Furthermore, the reference lines can also be used to carry out a correction of the detected measurement spectra, thereby compensating for influences in the measurement spectra that are caused as a result of variable ambient parameters.

Figure 7:
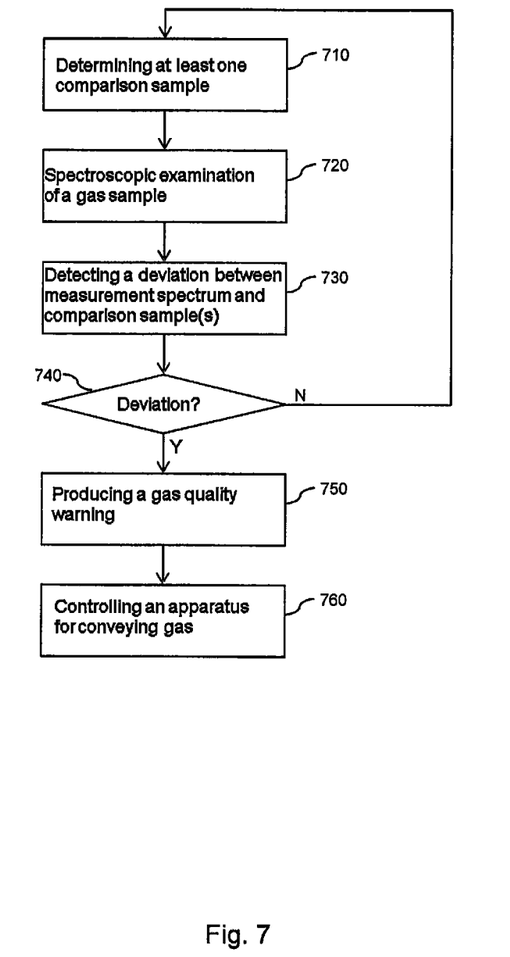
FIG. 7 shows a flow diagram for elucidating a method for gas quality monitoring in accordance with an exemplary embodiment of the invention.

FIG. 7 shows a flow diagram for elucidating a method for gas quality monitoring in accordance with an exemplary embodiment of the invention. The method can be carried out for example using the apparatus for gas quality monitoring explained above.

At step 710, at least one comparison pattern is determined. The at least one comparison pattern can be selected from a multiplicity of comparison patterns depending on one or more ambient parameters, e.g. depending on temperature, pressure, air humidity, or the like. The at least one comparison pattern may have been determined for example on the basis of measurement spectra classified as inconspicuous. By way of example, a multiplicity of measurement spectra can be detected under different ambient conditions and can be classified as inconspicuous in each case by an operator if an inadequate gas quality of the gas sample examined is not suspected. For this purpose, additional examinations can also be carried out by other analytical systems. In this case, a machine-based learning algorithm can also be used, e.g. on the basis of an artificial neural network (ANN).

In some scenarios, however, comparison patterns can also be learned during ongoing operation. For example, if the gas quality monitoring is carried out in conjunction with a ventilation installation for a vehicle, feedback from a vehicle occupant as to whether an odor nuisance has been perceived could be detected and used as a basis for the classification of a measurement spectrum recorded at this point in time as inconspicuous.

At step 720, a spectroscopic examination of a gas sample from a space to be monitored is carried out. The spectroscopic examination can be carried out in particular by Raman spectroscopy. The space to be monitored can be an interior of a vehicle or building or an air feed section of a ventilation installation. In some scenarios, however, the gas sample could also be taken in the open. If the gas quality monitoring is carried out in association with a process installation, the space to be monitored can be a feed section for a process gas, a process space of the process installation, or an exhaust gas section of the process installation.

The spectroscopic examination of the gas sample yields a measurement spectrum, such as e.g. one of the abovementioned measurement spectra 200, 310, 320, 410, 420, 510, 520, 610, 620. The measurement spectrum typically shows a wavelength-dependent intensity profile. The measurement spectrum can also be represented as an image, which is subdivided into a first region and a second region by the wavelength-dependent intensity profile, as has been explained for example in association with FIGS. 5A, 5B, 6A and 6B.

At step 730, a deviation between the measurement spectrum and the at least one comparison pattern is detected. The deviation can be detected by a comparison of a wavelength-dependent intensity of the measurement spectrum with at least one comparison intensity defined by the comparison pattern. Furthermore, as mentioned for step 720, the measurement spectrum can be represented in the form of an image, which is subdivided into a first region and a second region depending on a wavelength-dependent intensity. The deviation can then be detected by detecting an overlap of the first region and/or of the second region with at least one comparison region defined by the comparison pattern. Furthermore, at step 730, a severity of the deviation between the measurement spectrum and the at least one comparison pattern can also be detected. The severity can be quantified by a numerical value, for example, which enables a comparison with one or more threshold values.

At step 740, a check is carried out to establish whether a deviation was detected at step 730 or the deviation detected at step 730 has a specific minimum severity. This last can be done for example by comparing the severity of the deviation with a threshold value. If this is the case, the method is continued with step 750, as indicated by the branch "Y". Otherwise, the method can return to step 710, as indicated by the branch "N".

At step 750, a gas quality warning is produced. The gas quality warning indicates that there is the risk of an inadequate quality of a gas from which the gas sample examined at step 720 was taken. The gas quality warning can be produced as an optical and/or acoustic signal. Furthermore, the gas quality warning can also be produced as an electronic signal. The gas quality warning can also be produced depending on a severity—detected at step 730—of the deviation between the measurement spectrum and the at least one comparison pattern. By way of example, the gas quality warning can be produced in a plurality of levels, by the severity of the deviation being compared with one or more threshold values. In this regard, a first level of the gas quality warning could be produced if the severity of the deviation exceeds a first threshold value, and a second level of the gas quality warning could be produced if the severity of the deviation exceeds a higher second threshold value.

At step 760, an apparatus for conveying gas can then be controlled depending on the gas quality warning produced at step 750. By way of example, the conveyance of gas can be stopped in reaction to the gas quality warning, e.g. by valves or flaps being closed and/or a pump or a fan being deactivated. Furthermore, in reaction to the gas quality warning, measures for improving the gas quality can be initiated, e.g. by instigating venting of the space to be monitored.

As mentioned above, a machine-based learning algorithm can be used for learning the comparison patterns, e.g. on the basis of an ANN. The machine-based learning algorithm can be trained on the basis of previously classified measurement spectra and/or during ongoing operation. In the last-mentioned case, by way of example, an operator can provide the learning algorithm with feedback as to whether or not a gas quality warning produced was correct. Furthermore, a training measurement system which is based on additional sensor technology and/or analysis technology and identifies problematic gas compositions in a targeted manner can also be used for training the machine-based learning algorithm and for learning the comparison patterns. Such a training measurement system could be used only for training purposes, e.g. during commissioning, calibration or some other preconfiguration of the apparatus for gas quality monitoring. The training measurement system could therefore be based on more complex sensor technology than the apparatus for gas quality monitoring. Furthermore, during the training of the machine-based learning algorithm, it is also possible to carry out more complex analyses which e.g. typically cannot be performed in real time. The determination of the comparison patterns can be carried out by the machine-based learning algorithm beforehand for a multiplicity of apparatuses for gas quality monitoring, and the learning results obtained on the basis of one apparatus can be applied to other apparatuses.

Figure 8:
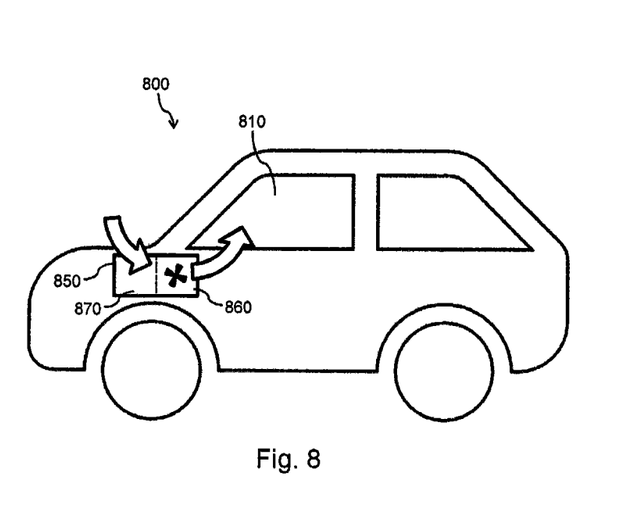
FIG. 8 illustrates an example of a scenario in which gas quality monitoring in accordance with an exemplary embodiment of the invention is used in a ventilation installation.

FIG. 8 illustrates an example of a scenario in which the gas quality monitoring described above is accordingly used in a ventilation installation. Specifically, FIG. 8 shows a motor vehicle 800 comprising a ventilation installation 850, which can be part of an air conditioning system, for example. However, it goes without saying here that this scenario can also be applied straightforwardly to a ventilation installation in some other type of vehicle, e.g. an aircraft, a watercraft, or a rail vehicle.

The ventilation installation 850 has an air feed section 870, via which air from outside is taken into the ventilation installation 850 and is then fed via an air conveying system 860 into an interior 810 of the motor vehicle 800. The air conveying system 860 can for example be based on a fan and furthermore comprise one or more flaps that can stop the feed of air from outside. This last is desirable, for example, if unpleasant odors occur in the vicinity of the motor vehicle 800 or the motor vehicle 800 is situated in a tunnel or a garage.

In the scenario in FIG. 8, the gas quality warning can be used to control the air conveying system 860. If the gas samples are taken from the air feed section 870, for example, the flaps of the air conveying system 860 can be closed in reaction to the gas quality warning in order to prevent low-quality air from being introduced into the vehicle interior 810. Furthermore, the gas samples can also be taken from the interior 810 of the motor vehicle 800. In this case, in reaction to the gas quality warning, the air conveying system 860 can be caused to feed air from outside into the interior 810 of the vehicle 800 in an intensified manner in order thus to improve the quality of the air in the interior 810. Furthermore, the gas quality warning can also be indicated to the driver or other occupants of the motor vehicle 800 in the form of an optical or acoustic signal. Furthermore, an air purification function of the ventilation installation 850 can also be activated. Such an air purification function can be based e.g. on a filter device.

Figure 9:
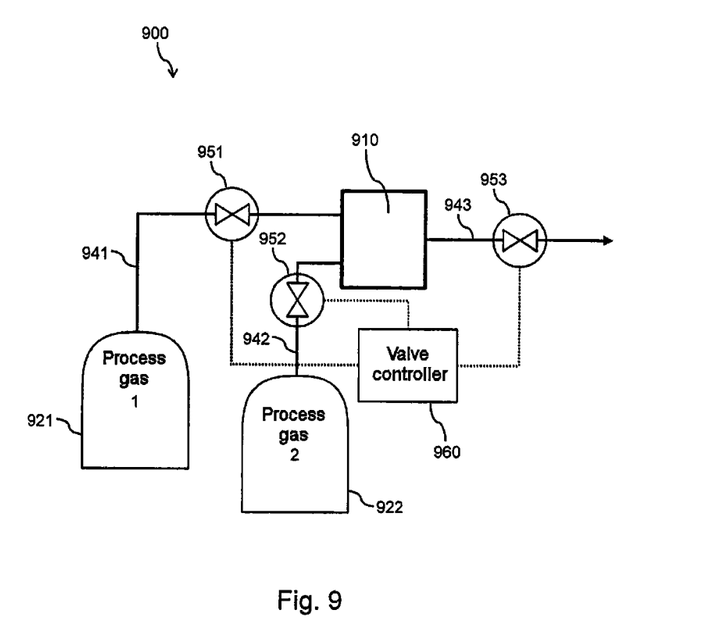
FIG. 9 illustrates an example of a scenario in which gas quality monitoring in accordance with an exemplary embodiment of the invention is used in a process installation.

FIG. 9 illustrates an example of a scenario in which the gas quality monitoring described above is accordingly used in a process installation 900. The process installation can serve for example for the production or processing of products. For example, products could be treated with one or a plurality of process gases in the process installation. Furthermore, a chemical reaction of one or a plurality of process gases could also take place in the process installation, e.g. in the context of combustion. In the example in FIG. 9, the process installation 900 comprises a process space 910, into which process gases from a first gas source 921 and from a second gas source 922 are fed. The process gases are fed via feed lines 941, 942, which are provided with controllable valves 951, 952. Furthermore, the process installation 900 also comprises an exhaust gas line 943, via which exhaust gases that arise during the processes in the process space 910 can be carried away. The exhaust gas line 943 is also provided with a controllable valve 953. The valves 951, 952, 953 are controlled by way of a valve controller 960. The feed lines 941, 942, the exhaust gas line 943, the valves 951, 952, 953 and the valve controller 960 form a gas conveying system of the process installation 900.

In the scenario in FIG. 9, the gas quality warning can be used to control the gas conveying system of the process installation 900. By way of example, if the gas samples are taken from the feed lines 941 or 942, the valves 951, 952 can be closed in reaction to the gas quality warning in order to prevent low-quality process gas from being introduced into the process space 910. Furthermore, gas samples can also be taken from the process space 910. In this case, in reaction to the gas quality warning, the valve 943 can be caused to be opened in order to remove low-quality gases from the process space 910. Furthermore, a gas purification function of the process installation 900 can also be activated. Such a gas purification function can be based e.g. on a chemical reaction in the process space 910. Alternatively or additionally, the gas purification can also be based on filtering. Furthermore, the gas quality warning can be indicated to an operator of the process installation 900 in the form of an optical or acoustic signal or can be used as a trigger for an automatic safety shutdown of the process installation 900.

It goes without saying that various modifications are possible for the exemplary embodiments described above. In this regard, the gas quality monitoring described is not restricted to ventilation installations or process installations, but rather could also be applied in diverse other fields. Moreover, the comparison patterns described herein can be modified or combined in various ways in order thus to generate new types of comparison patterns. Furthermore, as an alternative or in addition to obtaining the measurement spectra by Raman spectroscopy, other spectroscopic methods could also be used, e.g. infrared spectroscopy.

The invention claimed is:

1. A method for gas quality monitoring, comprising:
spectroscopic examination of a gas sample from a space to be monitored, wherein the spectroscopic examination yields a measurement spectrum extending over a wavelength range;
detecting a deviation of the measurement spectrum from at least one comparison pattern, wherein the measurement spectrum is represented as an image;
depending on the deviation that was detected, producing a gas quality warning; and
depending on the gas quality warning produced, controlling an apparatus for conveying gas into the space to be monitored and/or out of the space to be monitored,
wherein the detecting the deviation of the measurement spectrum comprises comparing the image of the measurement spectrum with the at least one comparison pattern.

2. The method of claim 1, comprising:
detecting at least one ambient parameter of the space to be monitored; and
selecting the at least one comparison pattern depending on the at least one ambient parameter that was detected.

3. The method of claim 2,
wherein the at least one ambient parameter comprises a temperature, a pressure and/or a moisture content.

4. The method of claim 1, comprising:
detecting the deviation by a comparison of a wavelength-dependent intensity of the measurement spectrum with at least one comparison intensity defined by the at least one comparison pattern.

5. The method of claim 1, comprising:
presenting the measurement spectrum as the image, which is subdivided into a first region and a second region depending on a wavelength-dependent intensity; and
detecting the deviation by detecting an overlap of the first region and/or of the second region with at least one comparison region defined by the at least one comparison pattern.

6. The method of claim 1, comprising:
detecting a severity of the deviation; and
producing the gas quality warning depending on the severity of the deviation that was detected.

7. The method of claim 1,
wherein the at least one comparison pattern describes shared properties of measurement spectra classified as inconspicuous.

8. The method of claim 1,
wherein the spectroscopic examination of the gas sample is carried out by Raman spectroscopy.

9. The method of claim 1, comprising:
determining the at least one comparison pattern by training a machine-based learning algorithm.

10. The method of claim 1,
wherein the apparatus comprises a ventilation installation and the space to be monitored is situated in an air feed section of the ventilation installation or in a space to be ventilated by way of the ventilation installation.

11. The method of claim 1,
wherein the apparatus comprises a process installation and the space to be monitored is situated in a feed section for a process gas used in the process installation or is situated in a process space of the process installation.

12. An apparatus for gas quality monitoring, comprising:
a spectrometer device for spectroscopic examination of a gas sample from a space to be monitored, wherein the spectroscopic examination yields a measurement spectrum extending over a wavelength range; and
an evaluation device configured to perform operations comprising:
detecting a deviation of the measurement spectrum from at least one comparison pattern, wherein the measurement spectrum is represented as an image; and
producing a gas quality warning depending on the deviation that was detected; and
depending on the gas quality warning produced, controlling an apparatus for conveying gas into the space to be monitored and/or out of the space to be monitored,
wherein the detecting the deviation of the measurement spectrum comprises comparing the image of the measurement spectrum with the at least one comparison pattern.

13. A ventilation installation, comprising:
an apparatus for conveying air into a space to be ventilated and/or out of the space to be ventilated; and
an apparatus for gas quality monitoring comprising:
a spectrometer device for spectroscopic examination of a gas sample from a space to be monitored, wherein the spectroscopic examination yields a measurement spectrum extending over a wavelength range, wherein the measurement spectrum is represented as an image; and an evaluation device configured to detect a deviation of the measurement spectrum from at least one comparison pattern based on comparing the image of the measurement spectrum with the at least one comparison pattern, and to produce a gas quality warning depending on the deviation that was detected, wherein the space to be monitored is situated in an air feed section of the ventilation installation or in the space to be ventilated, and wherein the apparatus for conveying air is controlled depending on the gas quality warning.

14. A process installation, comprising:

an apparatus for conveying gas into a process space of the process installation and/or out of the process space of the process installation; and an apparatus for gas quality monitoring comprising:

a spectrometer device for spectroscopic examination of a gas sample from a space to be monitored, wherein the spectroscopic examination yields a measurement spectrum extending over a wavelength range, wherein the measurement spectrum is represented as an image; and an evaluation device configured to detect a deviation of the measurement spectrum from at least one comparison pattern based on comparing the image of the measurement spectrum with the at least one comparison pattern, and to produce a gas quality warning depending on the deviation that was detected, wherein the space to be monitored is situated in a feed section for a process gas used in the process installation or is situated in the process space of the process installation, and wherein the apparatus for conveying gas is controlled depending on the gas quality warning.

\* \* \* \* \*

UNITED STATES PATENT AND TRADEMARK OFFICE
CERTIFICATE OF CORRECTION

PATENT NO. : 11,460,407 B2
APPLICATION NO. : 16/636281
DATED : October 4, 2022
INVENTOR(S) : Rode et al.

It is certified that error appears in the above-identified patent and that said Letters Patent is hereby corrected as shown below:

On the Title Page

Item (56) Reference Cited, OTHER PUBLICATIONS, Page 2, Column 2, Line 31:
Correct "http:///www.keison.co.uk/kane_auto1 shtml" to read
--http:///www.keison.co.uk/kane_auto1.shtml--

In the Specification

Column 6, Line 2:
Correct "wavelength A" to read --wavelength $\lambda$--

Column 6, Line 4:
Correct "wavelength A" to read --wavelength $\lambda$--

Signed and Sealed this
Tenth Day of January, 2023

Katherine Kelly Vidal
*Director of the United States Patent and Trademark Office*